United States Patent [19]
Kimura et al.

[11] Patent Number: 5,830,412
[45] Date of Patent: Nov. 3, 1998

[54] SENSOR DEVICE, AND DISASTER PREVENTION SYSTEM AND ELECTRONIC EQUIPMENT EACH HAVING SENSOR DEVICE INCORPORATED THEREIN

[75] Inventors: Tetsuo Kimura, Hachioji; Seiichi Tanaka, Yamato; Narimasa Takahashi, Koganei; Ryukichi Hashimoto, Sagamihara, all of Japan

[73] Assignee: Nittan Company Limited, Tokyo, Japan

[21] Appl. No.: 697,015

[22] Filed: Aug. 16, 1996

Related U.S. Application Data

[63] Continuation of Ser. No. 314,853, Sep. 29, 1994, abandoned.

[30] Foreign Application Priority Data

Sep. 30, 1993 [JP] Japan .................... 5-267979
Oct. 13, 1993 [JP] Japan .................... 5-280065
Apr. 27, 1994 [JP] Japan .................... 6-112291

[51] Int. Cl.⁶ ............................................. G01N 27/04
[52] U.S. Cl. .............................................. 422/90; 422/98
[58] Field of Search ............................... 422/94, 97, 98, 422/90; 340/577, 578, 579, 588, 589, 632, 633; 73/31.02, 31.06

[56] References Cited

U.S. PATENT DOCUMENTS

| | | | |
|---|---|---|---|
| 3,990,518 | 11/1976 | Hemme | 340/577 |
| 4,027,302 | 5/1977 | Healey et al. | 340/577 |
| 4,090,177 | 5/1978 | Urata et al. | 340/577 |
| 4,112,356 | 9/1978 | Toy | 73/31.06 |
| 4,219,806 | 8/1980 | Enemark | 73/31.06 |
| 4,250,829 | 2/1981 | Stephens | 440/1 |
| 4,319,229 | 3/1982 | Kirkov | 340/577 |
| 4,338,281 | 7/1982 | Treitinger et al. | 73/31.06 |
| 4,350,660 | 9/1982 | Robinson et al. | 422/90 |
| 4,381,922 | 5/1983 | Frey et al. | 422/98 |
| 4,410,632 | 10/1983 | Dilley et al. | 73/31.06 |
| 4,443,791 | 4/1984 | Risgin et al. | 73/31.06 |
| 4,453,131 | 6/1984 | Leary et al. | 422/90 |
| 4,458,239 | 7/1984 | Willey | 340/588 |
| 4,481,499 | 11/1984 | Arina et al. | 422/98 |
| 4,505,600 | 3/1985 | Suzuki et al. | 374/170 |
| 4,518,952 | 5/1985 | Tanaka et al. | 340/514 |
| 4,524,351 | 6/1985 | Kimura et al. | 340/629 |
| 4,525,700 | 6/1985 | Kimura et al. | 340/518 |
| 4,550,313 | 10/1985 | Kimura | 340/584 |
| 4,572,900 | 2/1986 | Wohltjen | 73/31.06 |
| 4,575,711 | 3/1986 | Suzuki et al. | 340/521 |
| 4,581,604 | 4/1986 | Kimura et al. | 340/521 |
| 4,638,304 | 1/1987 | Kimura et al. | 340/500 |
| 4,638,443 | 1/1987 | Kaneyasu | 364/497 |
| 4,639,605 | 1/1987 | Seki et al. | 340/578 |
| 4,640,628 | 2/1987 | Seki et al. | 340/577 |
| 4,644,333 | 2/1987 | Borendsz et al. | 73/31.06 |
| 4,668,939 | 5/1987 | Kimura et al. | 340/521 |
| 4,697,172 | 9/1987 | Kimura | 340/587 |
| 4,725,819 | 2/1988 | Sasaki et al. | 340/517 |
| 4,725,820 | 2/1988 | Kimura | 340/522 |
| 4,725,821 | 2/1988 | Kimura et al. | 340/529 |
| 4,727,359 | 2/1988 | Yuchi et al. | 340/588 |
| 4,733,224 | 3/1988 | Kimura | 340/521 |
| 4,744,038 | 5/1988 | Okayama | 340/577 |
| 4,745,399 | 5/1988 | Kimura | 340/521 |
| 4,774,502 | 9/1988 | Kimura | 340/501 |
| 4,785,284 | 11/1988 | Kimura | 340/505 |
| 4,792,433 | 12/1988 | Katsura et al. | 73/31.06 |
| 4,803,469 | 2/1989 | Matsushita | 340/577 |
| 4,831,361 | 5/1989 | Kimura | 340/506 |
| 4,884,222 | 11/1989 | Nagashima et al. | 340/577 |
| 4,887,072 | 12/1989 | Kimura et al. | 340/691 |
| 4,988,988 | 1/1991 | Kimura | 340/825.06 |
| 5,034,725 | 7/1991 | Sorenson | 340/632 |
| 5,217,692 | 6/1993 | Rump et al. | 422/98 |
| 5,250,170 | 10/1993 | Yagawara et al. | 73/31.06 |
| 5,376,924 | 12/1994 | Kubo et al. | 340/632 |

FOREIGN PATENT DOCUMENTS

| | | |
|---|---|---|
| 0022028 | 1/1981 | European Pat. Off. . |
| 61-116626 | 6/1986 | Japan . |
| 62-059834 | 3/1987 | Japan . |

*Primary Examiner*—Lorraine Spector
*Attorney, Agent, or Firm*—Leighton K. Chong

[57] ABSTRACT

A sensor device of the present invention is capable of surely detecting occurrence of a fire and a type of the fire. The sensor device includes a detection element made of an organic semiconductor element or an inorganic semiconductor element which is varied in characteristic value (i.e., resistance) thereof by both gas produced in a flaming-type fire and a smouldering-type fire and of which a variation in resistance by gas produced in a flaming-type fire is different in polarity from that by gas produced in a smouldering-type fire. A resistance of the detection element is extracted by a resistance extractor and then fed to a resistance decrease discriminator and a resistance increase discriminator, wherein a decrease or increase in resistance of the element is discriminated. An information output circuit outputs a predetermined signal depending on discrimination results provided by the discriminators, to thereby detect occurrence of a fire and/or a type of the fire.

10 Claims, 18 Drawing Sheets

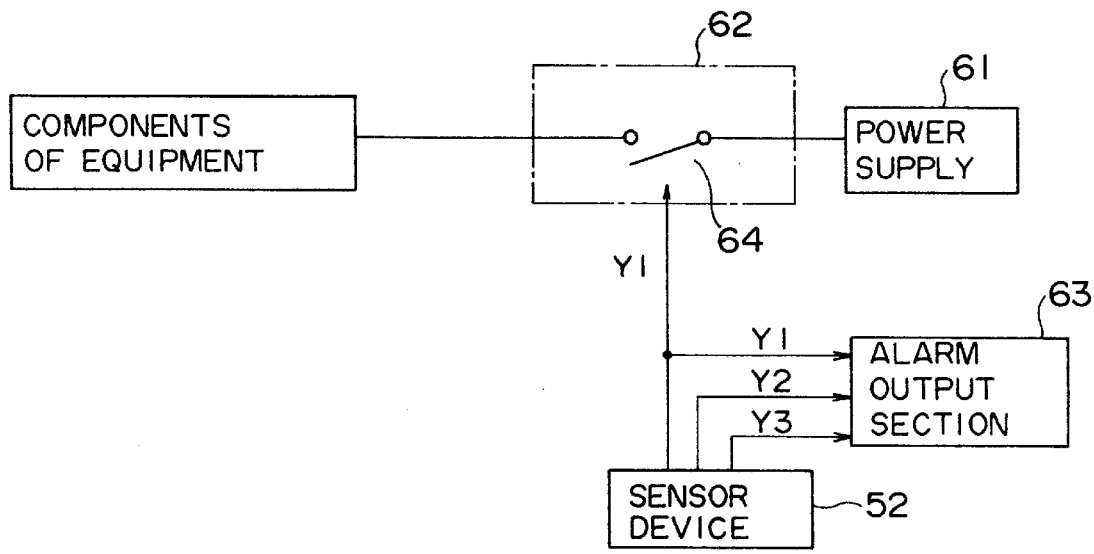

SENSOR DEVICE, AND DISASTER PREVENTION SYSTEM AND ELECTRONIC EQUIPMENT EACH HAVING SENSOR DEVICE INCORPORATED THEREIN

This is a continuation of U.S. patent application No. 08/314,853, filed on Sep. 29, 1994, now abandoned.

BACKGROUND OF THE INVENTION

This invention relates to a sensor device, and more particularly to a sensor device for detecting abnormality such as a fire or the like, and a disaster prevention system and an electronic equipment each having the sensor device incorporated therein.

A sensor device which has been conventionally used for detecting a disaster such as a fire or the like includes a heat sensor, a photoelectric smoke sensor, an ionization-type smoke sensor, a flame sensor and the like. Such a conventional sensor device is located at a predetermined position in a room of a building to constitute a disaster prevention system.

In general, fires are classified into a flaming-type fire and a smouldering-type(smoldering-type) fire. Unfortunately, the conventional sensor device fails to be satisfactorily applicable to both types. For example, it is known in the art that the above-described heat sensor, photoelectric smoke sensor, ionization-type smoke sensor, flame sensor generally exhibit characteristics as shown in Table 1.

TABLE 1

| Type of Fire | A | B | C | D |
|---|---|---|---|---|
| Flaming-Type Fire (Complete Combustion) | ○ | X | X | ○ |
| Flaming-Type Fire (Incomplete Combustion) | ○ | Δ | ○ | ○ |
| Smouldering-Type Fire | X | ○ | Δ | X |

A—Heat sensor
B—photoelectric smoke sensor
C—Ionization-type smoke sensor
D—Flame sensor
○—satisfactory detection
Δ—not too satisfactory detection
X—failure in satisfactory detection More particularly, the heat sensor and flame sensor each exhibit a satisfactory detection function with respect to a flaming-type fire but fail to exhibit a satisfactory detection function with respect to a smouldering-type fire. The photoelectric smoke sensor and ionization-type smoke sensor fail to satisfactorily detect a flaming-type fire of complete combustion.

Thus, when a disaster prevention system is to be constructed using any of the sensors described above, it is required to previously investigate a type of a fire which tends to occur in a circumstance at which the sensor is to be located, to thereby select an appropriate sensor. Thus, when the selected sensor is not suitable for use for the circumstance, it fails to detect a fire. Also, when an unexpected fire occurs even if a sensor which is suitably selected out of the above-described sensors is located in the circumstance, it fails to detect the fire.

SUMMARY OF THE INVENTION

The present invention has been made in view of the foregoing disadvantages of the prior art.

Accordingly, it is an object of the present invention to provide a sensor device which is capable of surely detecting abnormality such as a fire irrespective of a type of the abnormality.

It is another object of the present invention to provide a sensor device which is capable of discriminating a type or property of the abnormality such as a fire which has occurred.

It is a further object of the present invention to provide a disaster prevention system having a sensor device incorporated therein which is capable of surely detecting abnormality such as a fire irrespective of a type of the abnormality.

It is still another object of the present invention to provide a disaster prevention system having a sensor device incorporated therein which is capable of discriminating a type or property of the abnormality such as a fire which has occurred.

It is yet another object of the present invention to provide an electronic equipment having sensor device incorporated therein which is capable of surely detecting abnormality such as a fire irrespective of a type of the abnormality.

It is a still further object of the present invention to provide an electronic equipment having a sensor device incorporated therein which is capable of discriminating a type or property of the abnormality such as a fire which has occurred.

In accordance with the present invention, a sensor device is provided, which includes a detection element which is varied in predetermined characteristic value thereof by both electron acceptor gas and electron donor gas and in which a variation in predetermined characteristic value thereof by electron acceptor gas is different in polarity from that by electron donor gas, so that occurrence of abnormality and/or a property of the abnormality may be detected.

In accordance with the present invention, a sensor device is provided, which includes a detection element which is varied in predetermined characteristic value thereof by both first kind of gas produced during a flaming-type fire and second kind of gas produced during a smouldering-type fire and in which a variation in predetermined characteristic value thereof by the first kind of gas is different in polarity from that by the second kind of gas, so that occurrence of a fire and/or a property of the fire may be detected.

Organic semiconductor elements, such as metal substituted phthalocyanines, metal substituted phthalocyanines to which metal oxides are added, ion-doped polymers have the property as described above and can be used as the detection element of the present invention. Inorganic semiconductor elements, such as metal oxides having electric conductivity of a semiconductor level also have the property as described above and can also be used as the detection element of the present invention. Use of organic semiconductor elements or inorganic semicondutor elements as the detection element permits the sensor device to be significantly down-sized.

Further, in accordance with the present invention, a sensor device is provided, which includes a detection means having one or more detection elements constructed as described above, and a characteristic monitoring means for monitoring a variation in predetermined characteristic value of the detection elements to output predetermined abnormality information depending on the variation in predetermined characteristic value of the detection elements.

More particularly, the characteristic monitoring means is constructed so as to monitor resistances of the detection elements as the characteristic value of the detection elements to output abnormality (e.g. fire) occurrence information when the resistances are decreased or increased by a predetermined amount within a predetermined period of time. Such construction permits resistances of the elements to be varied in both a flaming-type fire and a smouldering-type fire, so that the sensor device may surely detect any type of fire.

In accordance with the present invention, the characteristic monitoring means includes a polarity detection function discriminating whether resistances of the elements are decreased or increased by a predetermined amount within a predetermined period of time, and is adapted to output abnormality property information corresponding to a polarity(decrease or increase) when resistances are decreased or increased by a predetermined amount within a predetermined period of time. Such construction permits a flaming-type fire and a smouldering-type fire to be surely distinguished from each other by detecting a polarity of each of the fires.

More particularly, in the case where the detection means comprises only one detection element, the characteristic monitoring means monitors, as the predetermined characteristic value, a decrease or increase of a resistance of this detection element. While, in the case where the detection means comprises a first element of a predetermined first conductive type and a second element of a predetermined second conductive type opposite to the first conductive type which are connected in series to each other, the characteristic monitoring means monitors, as the predetermined characteristic value, a decrease or increase of a resistance reflecting both resistances of the first and second elements connected in series. In the latter case, a variation in resistance when the elements are exposed to gas is larger than a variation in resistance in the former case, which permits occurrence of the abnormality(fire) and/or a property of the abnormality (fire) to be detected with increased sensitivity.

In accordance with the present invention, the information output means may be constructed so as to combine a detection result or signal provided by a conventional sensor with the discrimination results or signals provided by the resistance decrease discrimination means and resistance increase discrimination means to output the predetermined abnormality information. Such construction permits the abnormality information to be detected with high reliability.

In accordance with the present invention, the sensor device constructed as described above can be used for a disaster prevention system or an electronic equipment. In this case, an occurrence of fire can be surely and promptly detected even if any type of fire occurs, and further a type or property of fire can be detected, which permits the operator to promptly take proper steps depending on the detected type or property of fire.

These and other objects and many of the attendant advantages of the present invention will be readily appreciated as the same becomes better understood by reference to the following detailed description when considered in connection with the accompanying drawings.

BRIEF DESCRIPTION OF THE DRAWINGS

FIG. 18 is a block diagram showing details of the sensor device of FIG. 17; and

DESCRIPTION OF THE PREFFERED EMBODIMENTS

Now, the present invention will be described hereinafter with reference to the accompanying drawings.

Figure 1A:
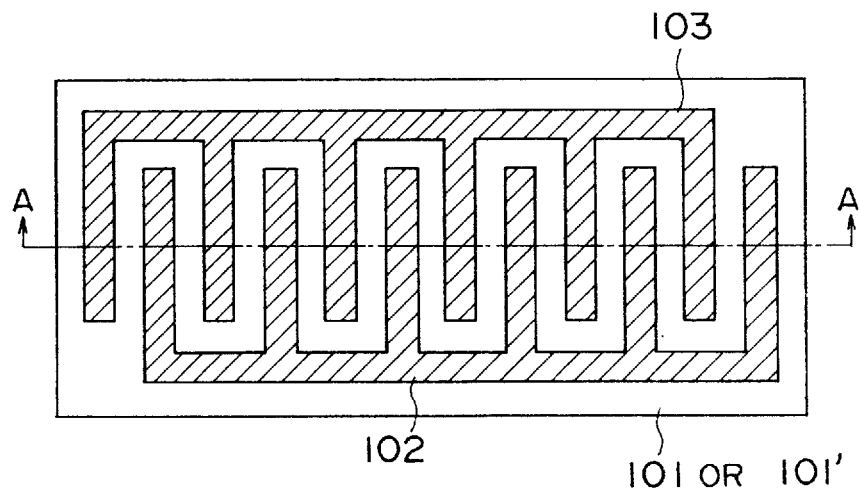
FIG. 1(a) is a plan view showing an example of a detection element suitable for use in the present invention.
Figure 1B:
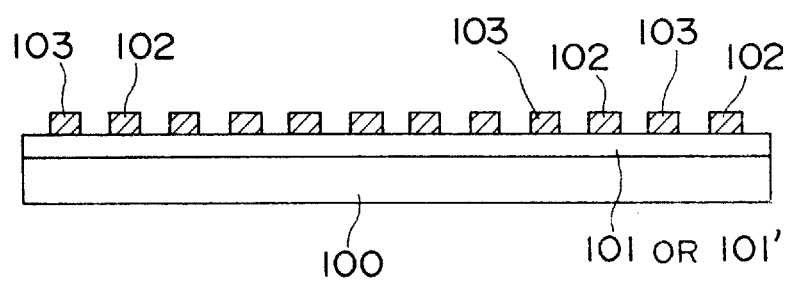
FIG. 1(b) is a sectional view taken along line A—A in FIG. 1(a)

FIGS. 1(a) and 1(b) illustrate an example of a detection element suitable for use in the present invention. The detection element illustrated comprises; for example, a substrate 100 made of glass, alumina, silicon or the like ; a metal phthalocyanine layer 101 containing metal such as copper, lead, cobalt, zinc or the like and formed on the substrate 100 by vapor deposition; and comb electrodes 102 and 103 formed on the phthalocyanine layer 101. Use of the metal phthalocyanine layer 101 makes this detection element function as an organic semiconductor element. The comb electrodes 102 and 103 each may be made of gold, platinum or the like. The substrate 100 may be formed into dimensions of about 3 mm in length, about 3 mm in width and about 1 mm in thickness and the phthalocyanine layer 101 is formed into a thickness as small as, for example, 10 nm to hundreds microns. The detection element may be further decreased in dimensions. Further, the electrodes 102 and 103 may be formed directly on the substrate 100 by vapor deposition, resulting in accomplishing down-sizing of the detection element.

In general, it is known that an organic semiconductor element made of phthalocyanines acts as a P-type semiconductor element and exposure of the element to nitrogen dioxide gas causes a decrease in resistance of the phthalocyanine layer 101. More particularly, nitrogen dioxide gas acts as electron acceptor gas on organic semiconductor such as lead phthalocyanine, nickel phthalocyanine or cobalt phthalocyanine which functions as a P-type type semiconductor, causing a decrease in resistance of the semiconductor.

Also, it is known that an organic semiconductor made by incorporating ruthenium oxide ($RuO_2$), palladium (Pd) or the like into metal phthalocyanine such as lead phthalocyanine, nickel phthalocyanine, cobalt phthalocyanine or the like acts as an n-type semiconductor and exposition of the semiconductor to electron acceptor gas causes an increase in resistance of the semiconductor. Thus, it will be noted that doping of a catalyst or a metal oxide into an organic semiconductor which inherently acts as a P-type semiconductor permits it to exhibit a function of an n-type semiconductor.

Alternatively, the detection element shown in FIGS. 1(a) and 1(b) may be constructed in such a manner that the substrate 100 is formed thereon with a metal oxide layer 101' having electric conductivity of a semiconductor level in place of the phthalocyanine layer 101 and then the two comb electrodes 102 and 103 are formed on the thus-formed metal oxide layer 101'. Such construction of the detection element permits it to act as an inorganic semiconductor element and permits it to exhibit substantially the same characteristics as the above-described organic semiconductor element.

More particularly, when the metal oxide layer 101' is formed of a material such as tin oxide, zinc oxide, iron oxide, a mixture thereof and the like, exposure of the metal oxide layer 101' to electron acceptor gas causes an increase in resistance of the metal oxide, so that the detection element may function as an n-type semiconductor. Also, when the metal oxide layer 101' is formed of a material such as copper oxide, chromium oxide, nickel oxide, a mixture thereof and the like, exposure of the metal oxide layer 101' to electron acceptor gas leads to a decrease in resistance of the metal oxide, so that the detection element may function as a P-type semiconductor.

When the substrate 100 is to be formed thereon with the metal oxide layer 101' in place of the phthalocyanine layer 101, to thereby provide an inorganic semiconductor element as described above, the metal oxide layer 101' may be formed into a thickness as small as, for example, 10 nm to hundreds microns as in the phthalocyanine layer 101. Also, the inorganic semiconductor element may be formed into a size of about 3 mm×3 mm as in the organic semiconductor element or into a smaller size. The electrodes 102 and 103 may be formed directly on the substrate 101 by vapor deposition, so that the inorganic semiconductor element may be significantly down-sized as in the organic semiconductor element described above.

The inventors made an experiment on the thus-formed detection elements, i.e., the P-type organic semiconductor element, n-type organic semiconductor element, P-type organic semiconductor element and n-type semiconductor element, wherein each of the detection elements was exposed to substantially the same gases as those produced in various kinds of fires, to thereby measure a variation in resistance of the elements. The results were as shown in Table 2.

TABLE 2

| Test Fire | P-Type Semiconductor | N-Type Semiconductor |
| --- | --- | --- |
| TF1 Timber Flaming Combustion | Decrease in Resistance | Increase in Resistance |
| TF2 Timber Smouldering Combustion | Increase in Resistance | Decrease in Resistance |
| TF3 Cotton Wick Smouldering Combustion | Increase in Resistance | Decrease in Resistance |
| TF4 Urethane Flaming Combustion | Decrease in Resistance | Increase in Resistance |
| TF5 n-Heptane Flaming Combustion | Decrease in Resistance | Increase in Resistance |
| TF6 Alcohol Flaming Combustion | Decrease in Resistance | Increase in Resistance |
| Paper Flaming Combustion | Decrease in Resistance | Increase in Resistance |
| Paper smouldering Combustion | Increase in Resistance | Decrease in Resistance |

From the experimental results shown in Table 2, it was found that when the detection element is of a P-type semiconductor, exposure of the detection element to gas produced by a flaming-type fire causes a decrease in resistance of the element, whereas the exposure to gas produced by a smouldering-type fire causes an increase in resistance of the element. Also, the results shown in Table 2 indicate that exposure of the detection element of an n-type semiconductor to gas produced by a flaming-type fire leads to an increase in resistance of the element, whereas the exposure to gas produced by a smouldering-type fire causes a decrease in resistance of the element. Thus, it will be noted that gas produced by a flaming-type fire substantially acts as electron acceptor gas on the detection elements, whereas gas produced by a smouldering-type fire substantially acts as an electron donor gas on the detection elements.

Figure 2:
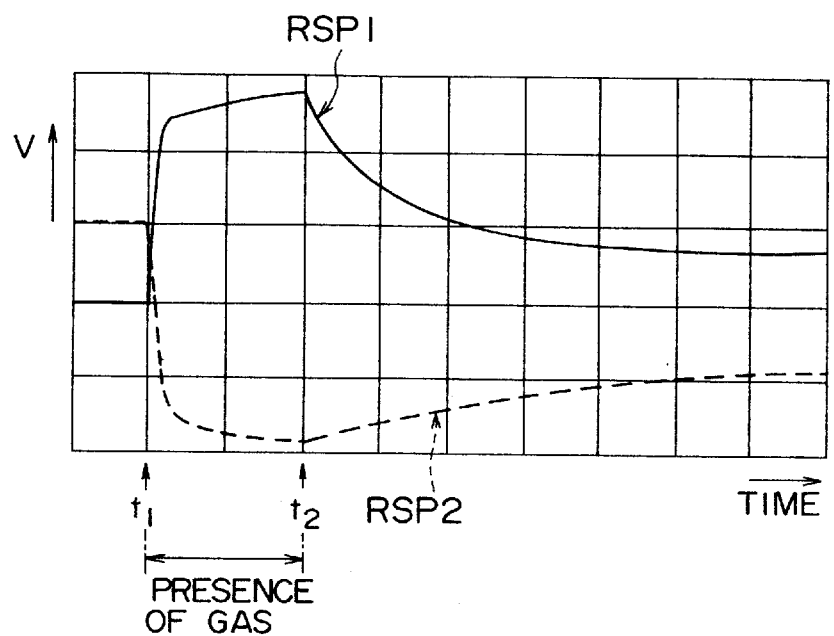
FIG. 2(a) is a graphical representation showing response characteristics of a detection element with respect to electron acceptor gas and electron donor gas.
FIG. 2(b) is a circuit diagram showing an electric circuit which may be used for obtaining the response characteristics shown in FIG. 2(a)
Figure 2:
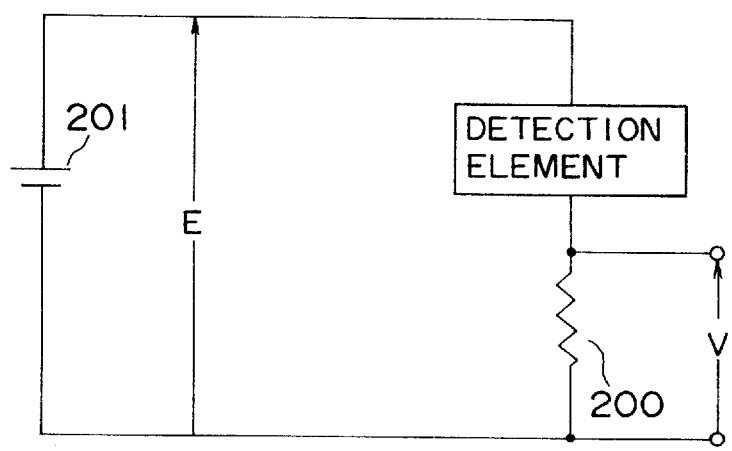

FIG. 2(a) shows response characteristics of the detection element functioning as the P-type semiconductor with respect to electron acceptor gas and electron donor gas, wherein the response characteristics of the detection element with respect to electron acceptor gas are designated at RSP1 and those with respect to electron donor gas are designated at RSP2. The response characteristics shown in FIG. 2(a) were obtained by means of a circuit constructed as shown in FIG. 2(b). In the circuit of FIG. 2(b), the detection element is connected in series to a resistor 200, and a voltage E of a predetermined level is applied to the detection element and resistor 200 from a power supply 201. Thus, the response characteristics RSP1, RSP2 were obtained by measuring a variation in resistance of the detection element functioning as the P-type semiconductor in the form of a voltage drop V of the resistor 200 when the detection element is exposed to electron acceptor gas, electron donor gas, respectively, from time t1 to time t2. It will be noted that the response characteristics RSP1 and RSP2 of FIG. 2(a) indicate that electron acceptor gas and electron donor gas each cause a variation in resistance of the detection element, however, a variation of resistance of the detection element by electron acceptor gas is caused to be different in polarity from that by electron donor gas.

The present invention has been made taking notice of the experimental results that the detection elements, i.e., organic semiconductor element and inorganic semiconductor element each are varied in resistance in both a flaming-type fire and a smouldering-type fire and a variation in resistance of each of the detection elements in a flaming-type fire is caused to be different in polarity from that in a smouldering-type fire.

Figure 3:
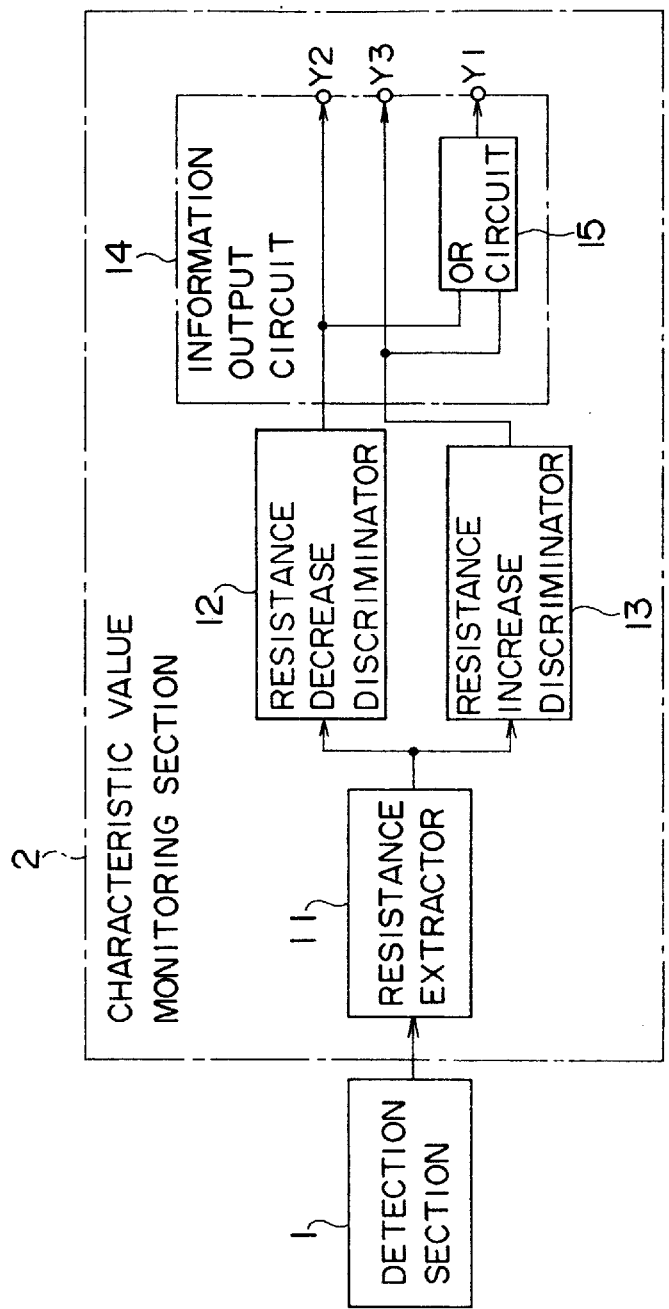
FIG. 3 is a block diagram showing a general construction of a sensor device according to the present invention.

Referring now to FIG. 3, a sensor device according to the present invention is illustrated. The sensor device of the present invention shown in FIG. 3 includes a detection section 1 comprising at least one organic semiconductor element or inorganic semiconductor element and a characteristic monitoring section 2 for monitoring a variation in predetermined characteristic value of the detection section 1 to output predetermined abnormal information depending on the variation in characteristic value of the detection section 1.

In the sensor device of FIG. 3, the characteristic value monitoring section 2 includes a resistance extractor 11 for extracting a resistance of a predetermined portion of the detection section 1 as the above-described predetermined characteristic value, a resistance decrease discriminator 12 for discriminating a decrease in resistance based on the extracted resistance, a resistance increase discriminator 13 for discriminating an increase in resistance based on the extracted resistance, and an information output circuit 14 for outputting predetermined abnormal information depending on a result of discrimination by each of the resistance decrease discriminator 12 and resistance increase discriminator 13.

The information output circuit 14 includes an OR circuit 15 for taking a logical OR of the discrimination result of the resistance decrease discriminator 12 and that of the resistance increase discriminator 13, and is adapted to output the logical OR from the OR circuit 15 in the form of an abnormality occurrence signal (fire occurrence signal) Y1, output the discrimination result of the resistance decrease discriminator 12 in the form of a first abnormal property signal (first fire property signal) Y2 and output the discrimination result of the resistance increase discriminator 13 in the form of a second abnormal property signal (second fire property signal) Y3.

Figure 4:
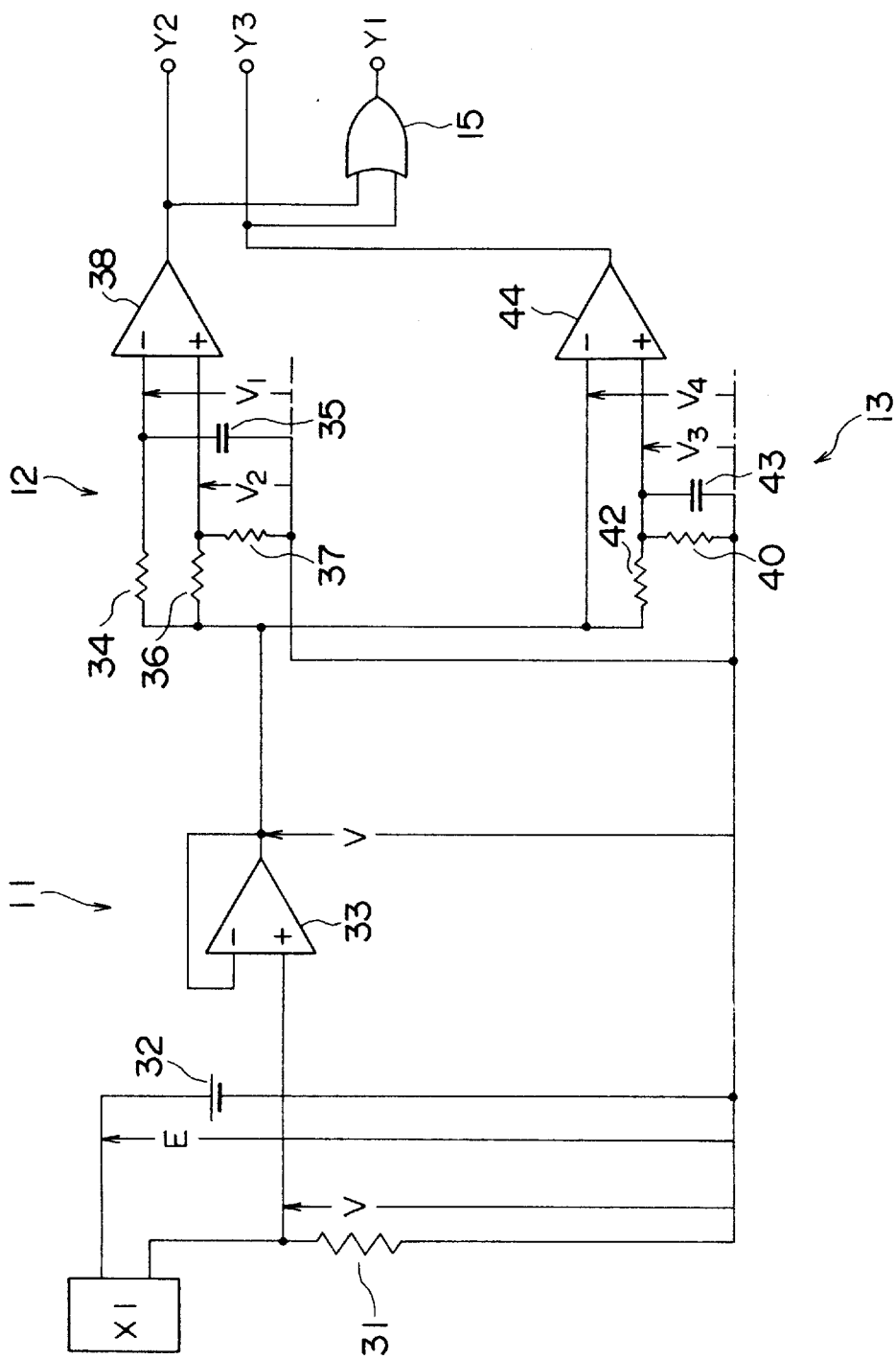
FIG. 4 is a circuit diagram showing a first embodiment of the sensor device of the present invention shown in FIG. 3.

FIG. 4 shows a first embodiment of the sensor device of the present invention shown in FIG. 3. A sensor device of the illustrated embodiment is so constructed that a single detection element X1 is used for a detection section 1. An element exhibiting a function as a P-type semiconductor such as lead phthalocyanine which is an organic semiconductor, nickel oxide which is a metal oxide or the like may be used for the detection element X1. Alternatively, an element exhibiting a function of an n-type semiconductor such as phthalocyanine (organic semiconductor) in which ruthenium oxide and palladium are incorporated or tin oxide which is a metal oxide may be conveniently used for this purpose.

The resistance extractor 11 includes a resistor 31 connected in series to the detection element X1, a power supply 32 for providing voltage E of a predetermined level to the detection element X1 and resistor 31, and a buffer 33, and is adapted to extract a resistance of the detection element X1 as a voltage V across the resistor 31. The buffer 33 is provided for the purpose of subjecting the voltage V across the resistor 31 to impedance conversion for output because the detection element X1 has an extremely high impedance.

The resistance decrease discriminator 12 includes an RC time constant circuit comprising, for example, a resistor 34 and a capacitor 35, a voltage dividing circuit comprising resistors 36 and 37, and a comparator 38 for outputting a discrimination result wherein a logical value is "1" when a voltage V1 across the capacitor 35 which is applied to a negative terminal of the comparator 38 is lower than a voltage V2 across the resistor 37 which is applied to a positive terminal of the comparator 38.

Resistances R1, R2 and R3 of the resistors 34, 36, 37 and a capacitance C1 of the capacitor 35 each are set at a suitable value so that the resistance decrease discriminator 12 may detect only an increase in voltage V by a predetermined amount or more within a predetermined period of time $\Delta t$, that is, may detect only a decrease in resistance of the detection element X1 by a predetermined amount $\Delta R$ or more within the predetermined period of time $\Delta t$. More particularly, the resistances R1, R2 and R3 and capacitance C1 each are set to be a value which permits the voltages V1 and V2 to meet such a relationship as shown in FIG. 5(b) with respect to such a voltage v as shown in FIG. 5(a) which is transiently increased by the predetermined amount $\Delta V$ or more within the predetermined period of time $\Delta t$, permits the voltages V1 and V2 to constantly meet a relationship of V2<V1 as shown in FIG. 6(b) with respect to such a voltage V as shown in FIG. 6(a) which requires the predetermined period of time $\Delta t$ or more for an increase in voltage by the predetermined amount $\Delta V$, and permits the voltages V1 and V2 to constantly meet the relationship of V2<V1 as shown in FIG. 7(b) with respect to such a voltage as shown in FIG. 7(a) which is not increased by the predetermined amount $\Delta V$ or more.

Figure 8:
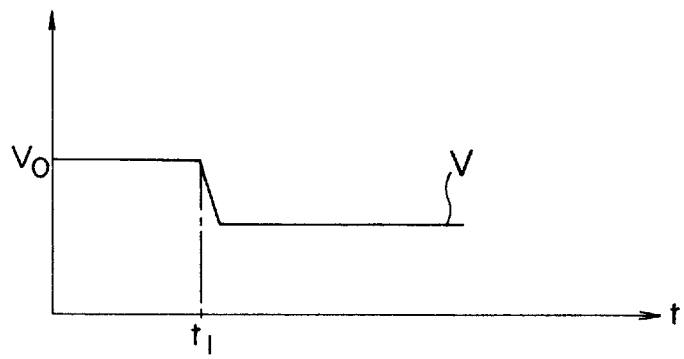
FIGS. 8(a) to 8(c) each are a graphical representation showing still another example of operation of a resistance decrease discriminator.
Figure 8:
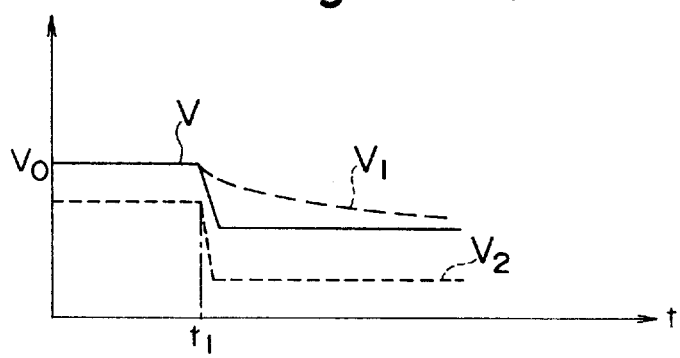

When the voltage V is decreased in such a manner as shown in FIG. 8(a) (i.e., when the detection element X1 is increased in resistance), the voltage V1 is kept constantly higher than the voltage V2 irrespective of the resistances R1, R2 and R3 of the resistors 34, 36 and 37 and the capacitance C1 of the capacitor 35, as shown in FIG. 8(b).

Figure 5A:
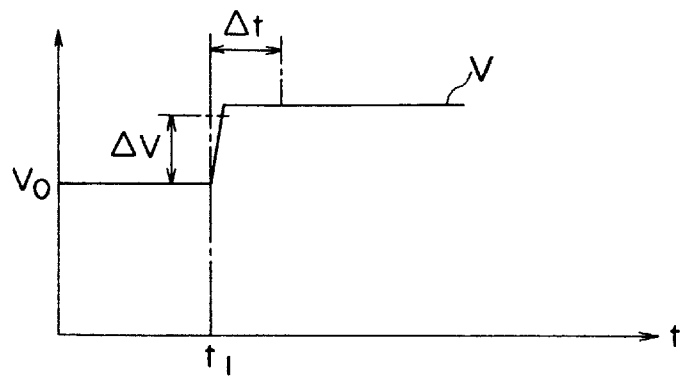
FIGS. 5(a) to 5(c) each are a graphical representation showing an example of operation of a resistance decrease discriminator.
Figure 5B:
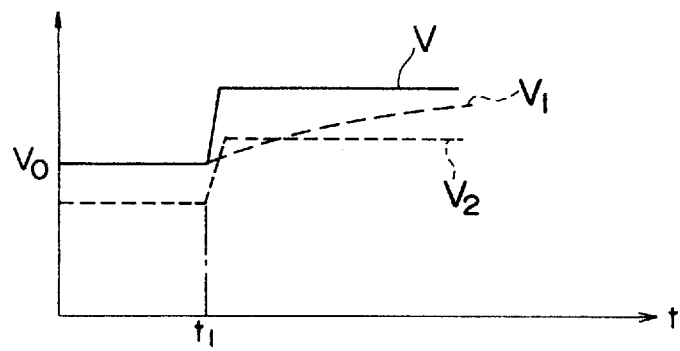
Figure 5C:

Setting of each of the resistances R1, R2 and R3 of the resistors 34, 36 and 37 and the capacitance C1 of the capacitor 35 at a suitable value as described above permits the voltage V2 to be higher than the voltage V1 only when the voltage V is increased by the predetermined amount $\Delta V$ or more within the predetermined period of time $\Delta t$ as shown in FIG. 5(a), resulting in the comparator 38 outputting a logical value "1" only in this case (FIG. 5(c)).

Figure 6A:
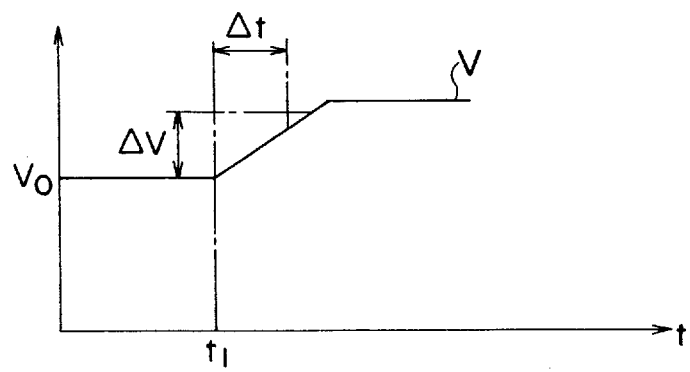
FIGS. 6(a) to 6(c) each are a graphical representation showing another example of operation of a resistance decrease discriminator.
Figure 6B:
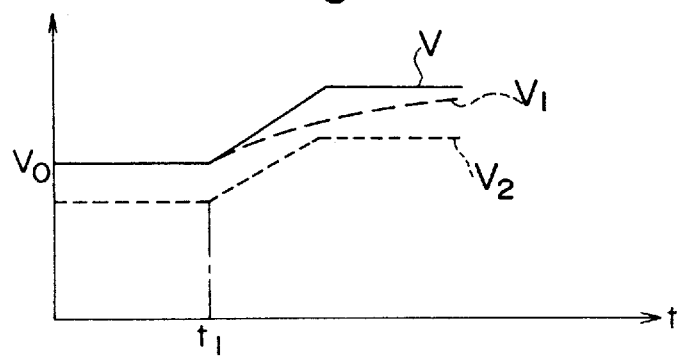
Figure 6C:
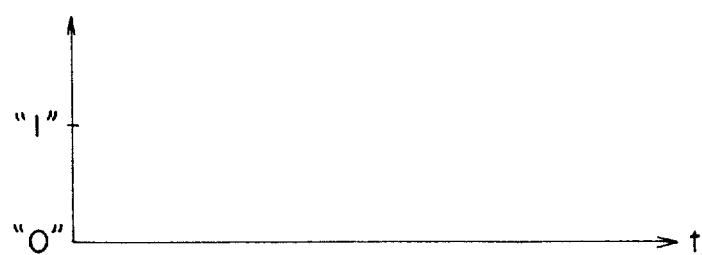
Figure 7A:
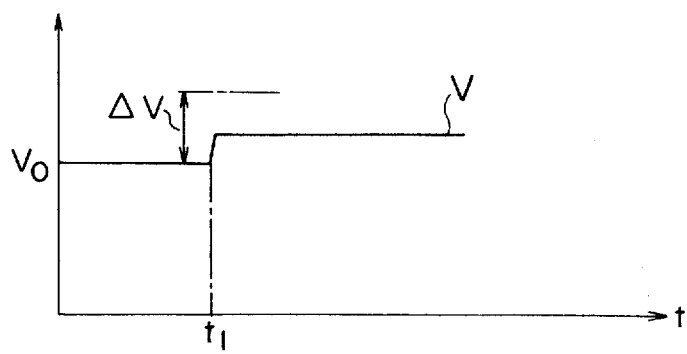
FIGS. 7(a) to 7(c) each are a graphical representation showing a further example of operation of a resistance decrease discriminator.
Figure 7B:
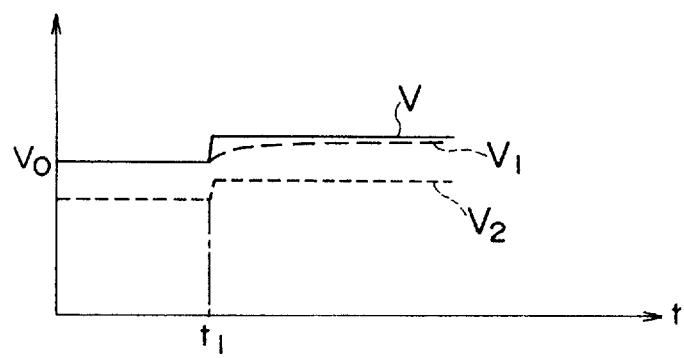
Figure 7C:
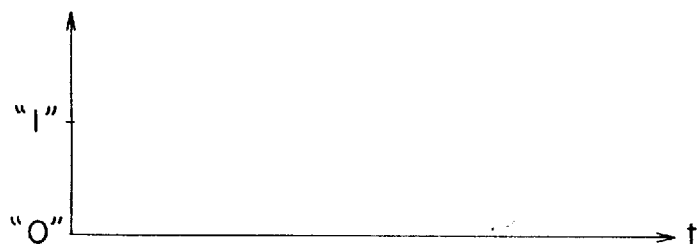

More particularly, when the voltage V is not increased by the predetermined amount $\Delta V$ or more within the predetermined period of time $\Delta t$ as shown in FIG. 6(a), the voltage V2 is kept constantly lower than the voltage V1, so that the comparator 38 is kept from outputting the logical value "1". This results in the comparator 38 being kept from outputting the logical value "1" as shown in FIG. 6(c), to thereby prevent the detection element from carrying out erroneous detection, when the voltage V is slowly increased for aged deterioration, or when the voltage V is slowly increased for restoration after the element has been released from being exposed to electron donor gas. Further, the comparator 38, as shown in FIG. 7(c), is kept from outputting the logical value "1" also when the voltage V is slightly increased due to any noise (i.e., when the voltage V is varied as shown in FIG. 7(a)), resulting in erroneous detection by the sensor element being effectively prevented.

Figure 8C:
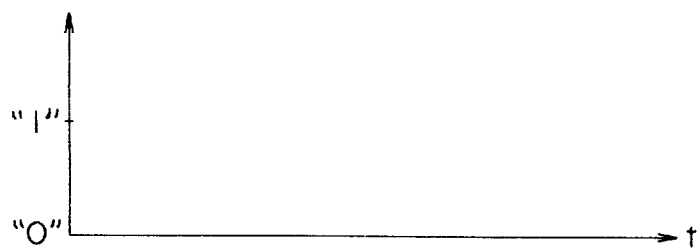

In addition, the voltage V2 is kept constantly lower than the voltage V1 as shown in FIG. 8(b) also when the voltage V is decreased as shown in FIG. 8(a), so that the comparator 38 may be kept from outputting a signal of a logical value "1" (FIG. 8(c)).

Referring to FIG. 4, the resistance increase discriminator 13 includes an RC time constant circuit comprising a resistor 40, a resistor 42 and a capacitor 43, and a comparator 44 for outputting a discrimination result wherein a logical value is "1" when a voltage V3 across the resistor 40 (i.e, a voltage across the capacitor 43) which is applied to a positive terminal of the comparator 43 is higher than a voltage V (V4) which is applied to a negative terminal of the comparator 44.

Resistances R5 and R6 of the resistors 40 and 42 and a capacitance C2 of the capacitor 43 each are set at a suitable value which permits the resistance decrease discriminator 13 to detect only a decrease in voltage V by a predetermined amount ΔV' or more within a predetermined period of time Δt, that is, only an increase in resistance of the detection element X1 by a predetermined amount ΔR' or more within the predetermined period of time Δt. More particularly, the resistances R5 and R6 and capacitance C2 each are set to be a value which permits the voltages V3 and V4 to meet such a relationship as shown in FIG. 9(b) with respect to such a voltage v as shown in FIG. 9(a) which is transiently decreased by the predetermined amount ΔV' or more within the predetermined period of time Δt, permits the voltages V3 and V4 to constantly meet a relationship of V3<V4 as shown in FIG. 10(b) with respect to such a voltage V as shown in FIG. 10(a) which requires the predetermined period of time Δt or more for a decrease in voltage by the predetermined amount ΔV', and permits the voltages V3 and V4 to constantly meet a relationship of V3<V4 as shown in FIG. 11(b) with respect to such a voltage V as shown in FIG. 11(a) which is not decreased by the predetermined amount ΔV' or more.

Figure 12A:
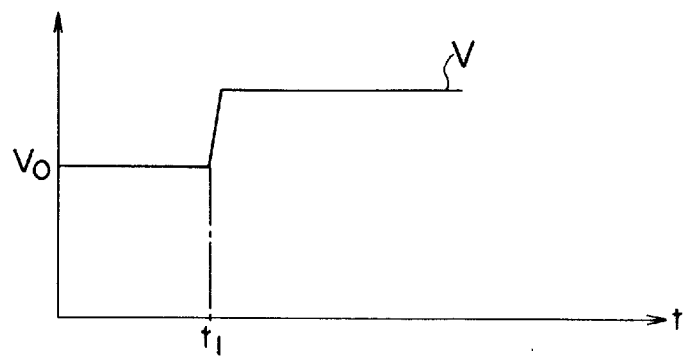
FIGS. 12(a) to 12(c) each are a graphical representation showing still another example of operation of a resistance increase discriminator.
Figure 12B:
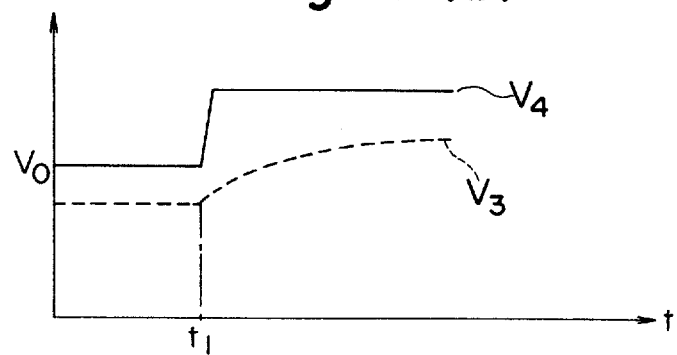

When the voltage V is increased in such a manner as shown in FIG. 12(a) (i.e., when the element X1 is decreased in resistance), the voltage V4, as shown in FIG. 12(b), is kept constantly higher than the voltage V3 irrespective of the resistances R5 and R6 of the resistors 40 and 42 and the capacitance C2 of the capacitor 43.

Figure 9A:
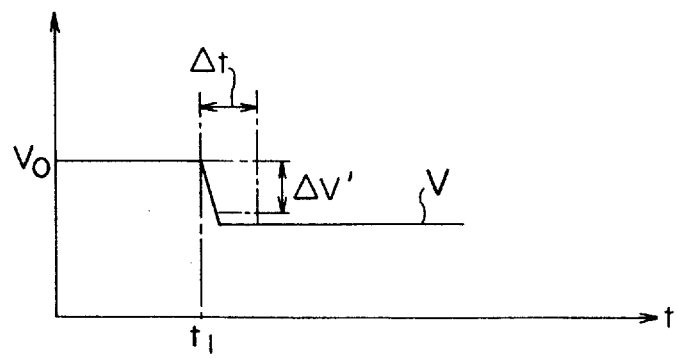
FIGS. 9(a) to 9(c) each are a graphical representation showing an example of operation of a resistance increase discriminator.
Figure 9B:
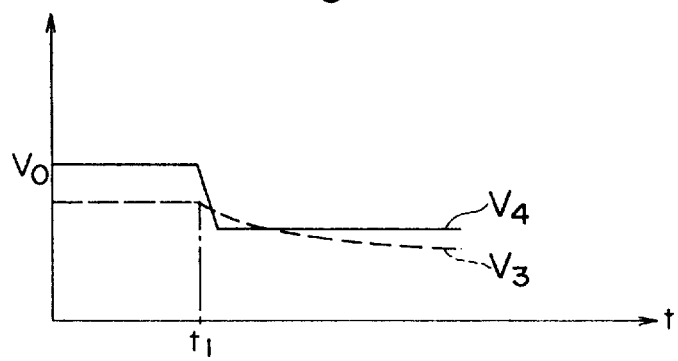
Figure 9C:
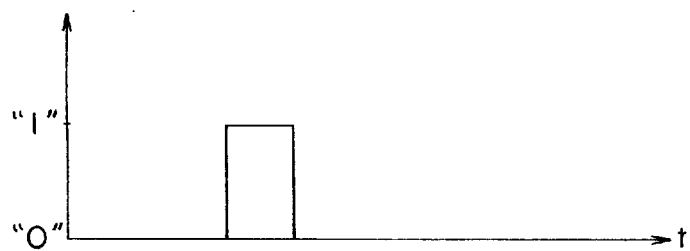

Such setting of each of the resistances R5 and R6 of the resistors 40 and 42 and the capacitance C2 of the capacitor 43 at such a suitable value as described above permits the voltage V3 applied to the positive terminal of the comparator 44 to be higher than the voltage V4 only when the voltage V is decreased by the predetermined amount ΔV' or more within the predetermined period of time Δt as shown in FIG. 9(a), resulting in the comparator 44 outputting a logical value "1" only in this case (FIG. 9(c)).

Figure 10A:
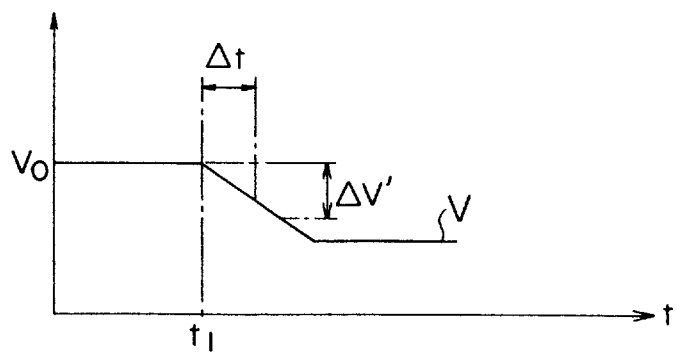
FIGS. 10(a) to 10(c) each are a graphical representation showing another example of operation of a resistance increase discriminator.
Figure 10B:
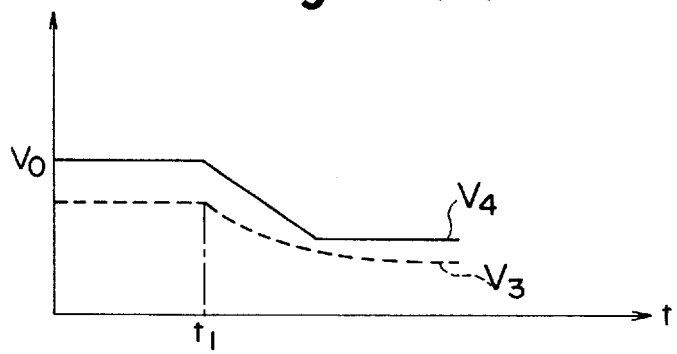
Figure 10C:
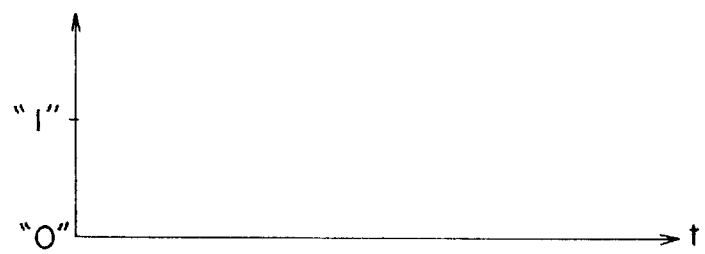
Figure 11A:
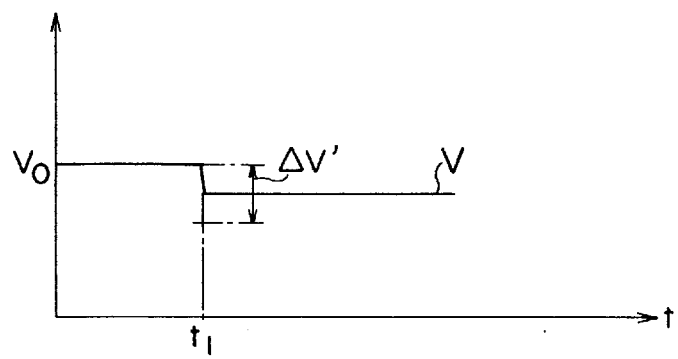
FIGS. 11(a) to 11(c) each are a graphical representation showing a further example of operation of a resistance increase discriminator.
Figure 11B:
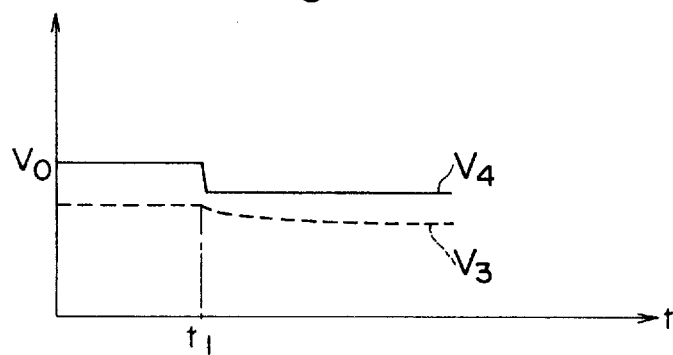
Figure 11C:
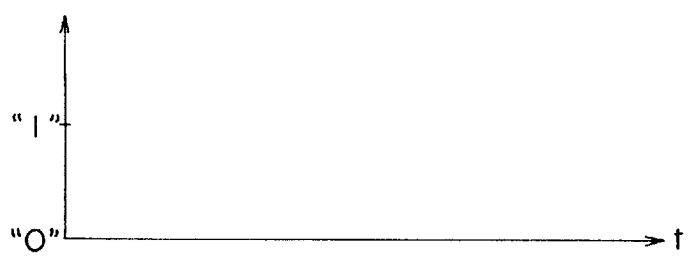

More particularly, when the voltage V is not decreased by the predetermined amount ΔV' or more within the predetermined period of time Δt as shown FIG. 10(a), the voltage V3 is kept lower than the voltage V4, so that the comparator 44 is kept from outputting the logical value "1". This results in the comparator 44 being kept from outputting the logical value "1" as shown in FIG. 10(c), to thereby prevent the detection element from carrying out any erroneous detection, when the voltage V is slowly decreased for aged deterioration, or for restoration after the element has been released from being exposed to electron acceptor gas. Further, the comparator 44, as shown in FIG. 11(c), is kept from outputting the logical value "1" also when the voltage V is slightly decreased due to any noise (i.e., when the voltage V is varied as shown in FIG. 11(a)), resulting in erroneous detection by the detection element being effectively prevented.

Figure 12C:
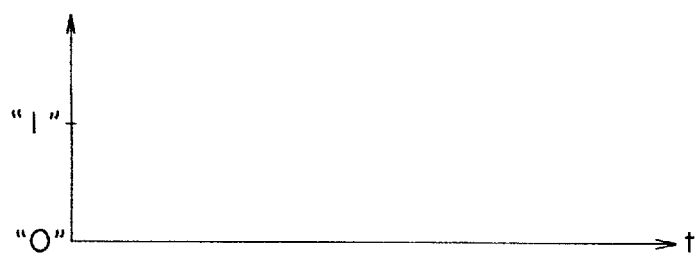

In addition, the voltage V3 is constantly kept lower than the voltage V4 as shown in FIG. 12(b) also increased as shown is increased as shown in FIG. 12(a), so that the comparator 44 may be kept from outputting the logical value "1" (FIG. 12(c)).

Now, the manner of operation of the sensor device of the illustrated embodiment constructed as described above will be described hereinafter with reference to FIG. 4.

In order to ensure that the sensor device of the illustrated embodiment properly operates, the detection section 1 is located at such a position that the detection element (organic semiconductor element or inorganic semiconductor element) X1 is exposed to combustion gas produced by abnormality or a fire.

When an organic semiconductor element functioning as a P-type semiconductor such as lead phthalocyanine or the like is used for the detection element X1, or when an inorganic semiconductor element (a metal oxide element) functioning as a P-type semiconductor such as nickel oxide or the like is used for the detection element X1, exposure of the detection element X1 to electron acceptor gas contained in combustion gas produced by a flaming-type fire causes a resistance of the element X1 to be rapidly decreased, so that the voltage V across the resistor 31 of the resistance extractor 11 may be rapidly increased as indicated at the response characteristics RSP1 in FIG. 2(a).

More particularly, supposing that a voltage V induced across the resistor 31 when the detection element X1 is not exposed to any gas is indicated at V0, the voltage V across the resistor 31, when the element X1 is exposed to, for example, electron acceptor gas produced by a flaming-type fire at time t1, starts at the voltage V0 and is increased by the predetermined amount ΔV or more within the predetermined period of time Δt as shown in FIG. 5(a). The voltage V across the resistor 31 is applied to both the resistance decrease discriminator 12 and resistance increase discriminator 13 through the buffer 33.

At the time of such rising of the response characteristics RSP1, the voltage V1 across the capacitor 35 of the RC time constant circuit and the voltage V2 across the resistor 37 of the voltage dividing circuit are varied in the resistance decrease discriminator 12 as shown in FIG. 5(b), so that the comparator 38 outputs a signal of the logical value "1" as shown in FIG. 5(c). This results in the information output circuit 14 generating the abnormality occurrence signal (fire occurrence signal) Y1 and the first abnormal property signal (first fire property signal) Y2. At this time, an output of the comparator 44 of the resistance increase discriminator 13 has a logical value "0", therefore, the information output circuit 14 is kept from generating the second abnormality signal (second fire property signal) Y3.

When the detection element X1 is caused not to be exposed to electron acceptor gas at time t2, the voltage across the resistor 31 falls or is restored toward the voltage V0 as indicated at the response characteristics RSP1 in FIG. 2(a). However, such falling or restoration is slow, so that the voltage is not decreased by the predetermined amount ΔV' or more within the predetermined period of time Δt, to thereby prevent erroneous operation of the resistance increase discriminator 13. Thus, none of the signals Y1, Y2 and Y3 are generated during restoration of the response characteristics RSP1.

Thus, it will be noted that the sensor device of the illustrated embodiment surely detects exposure of the detection element X1 to electron acceptor gas contained in combustion gas produced by a flaming-type fire, to thereby rapidly output the fire occurrence signal Y1 and first fire property signal Y2.

On the other hand, when the detection element X1 is exposed to electron donor gas contained in combustion gas produced by a smouldering-type gas, the detection element X1 is rapidly increased in resistance, so that the voltage V across the resistor 31 of the resistance extractor 11 is rapidly decreased as indicated at the response characteristics RSP2 in FIG. 2(a). More particularly, supposing that a voltage V induced across the resistor 31 when the detection element X1 is not exposed to any gas is indicated at V0, the voltage V across the resistor 31, when the element X1 is exposed to, for example, electron donor gas produced by a smouldering-type fire at time t1, starts at V0 and decreased by the predetermined amount ΔV' or more within the predetermined period of time Δt as shown in FIG. 9(a). The voltage V across the resistor 31 is applied to the resistance decrease discriminator 12 and resistance increase discriminator 13 through the buffer 33.

At the time of such falling of the response characteristics RSP2, the voltage V3 across the capacitor 43 of the RC time constant circuit is varied in the resistance increase discriminator 13 as shown in FIG. 9(b), so that the comparator 44 outputs a signal of the logical value "1" as shown in FIG. 9(c). This results in the information output circuit 14 outputting the abnormality occurrence signal (fire occurrence signal) Y1 and second abnormal property signal (second fire property signal) Y3. At this time, an output of the comparator 38 of the resistance decrease discriminator 12 has a logical value "0", therefore, the comparator 38 is kept from outputting the first abnormal property signal (first fire property signal) Y2.

Also, when the detection element X1 is caused not to be exposed to electron donor gas at time t2, the voltage V3 across the capacitor 43 rises or is restored toward the voltage V0 as indicated at the response characteristics RSP2 in FIG. 2(a). However, such rising or restoration is slow, so that the voltage is not decreased by the predetermined amount ΔV or more within the predetermined period of time Δt, to thereby prevent erroneous operation of the resistance increase discriminator 12. Thus, none of the signals Y1, Y2 and Y3 are generated during restoration of the response characteristics RSP2.

Thus, it will be noted that the sensor device of the illustrated embodiment surely detects exposure of the detection element X1 to electron donor gas contained in combustion gas produced by a smouldering-type fire, to thereby rapidly output the fire occurrence signal Y1 and second fire property signal Y3.

As can be seen from the foregoing, the sensor device of the illustrated embodiment permits the fire occurrence signal Y1 to be generated whenever any type of fire (i.e., a flaming-type fire accompanied with complete combustion, a flaming-type fire accompanied with incomplete combustion, a smouldering-type fire) occurs, to thereby surely and effectively detect occurrence of the fires. Also, use of the P-type semiconductor such as a lead phthalocyanine element or a nickel oxide element for the detection element X1 permits the first fire property signal Y2 to be generated when a flaming-type fire occurs and permits the second fire property signal Y3 to be generated when a smouldering-type fire occurs, to thereby effectively detect a type of the fire occurring.

Also, the sensor device of the illustrated embodiment includes the organic semiconductor element or inorganic semiconductor element which can be down-sized and the signal processing circuit which can be constructed in a compact and simplified manner, resulting in being down-sized and decreased in manufacturing cost as a whole.

Figure 13:
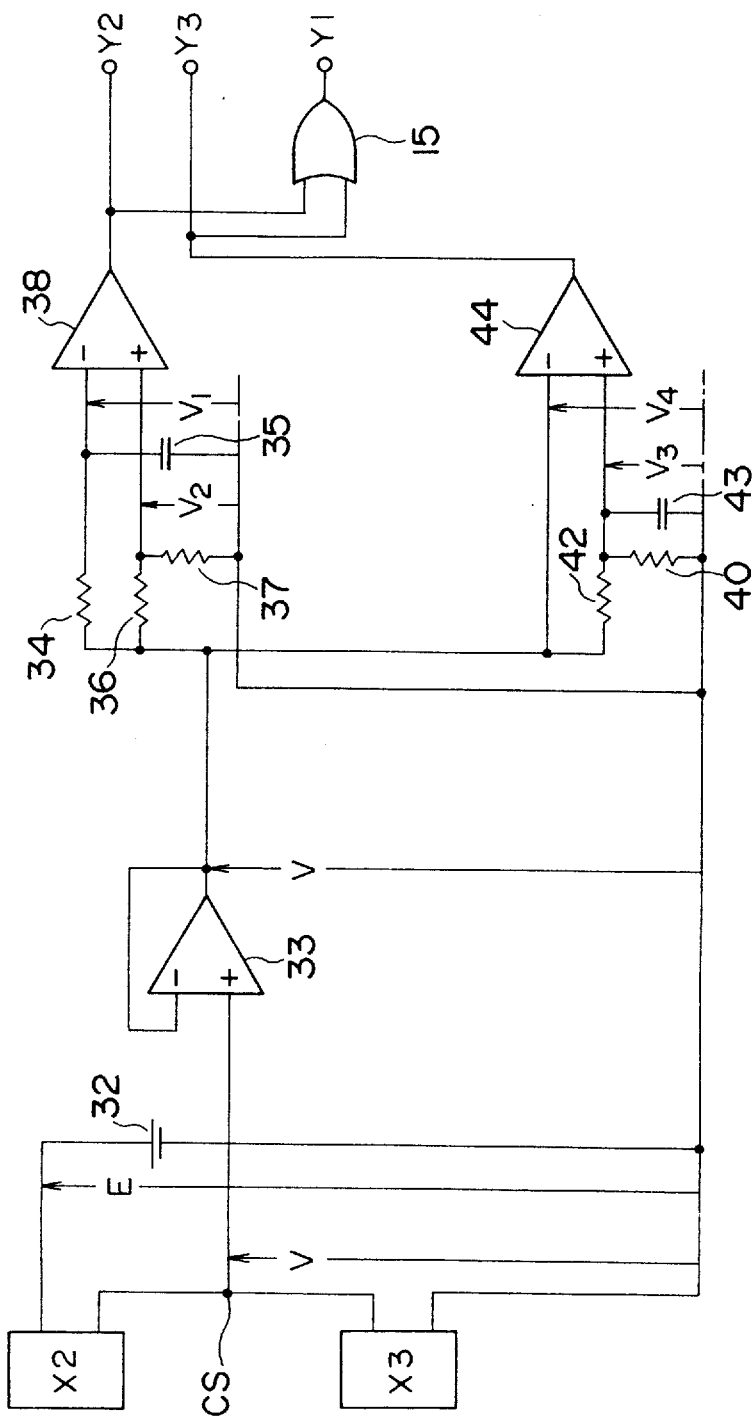
FIG. 13 is a circuit diagram showing a second embodiment of the sensor device of the present invention shown in FIG. 3.

Referring now to FIG. 13, a second embodiment of the sensor device of the present invention shown in FIG. 3 is illustrated. In the sensor device shown in FIG. 13, a detection section 1 includes two detection elements comprising a first detection element X2 functioning as a P-type semiconductor and a second detection element X3 functioning as an n-type semiconductor. The first and second detection elements X2 and X3 are connected in series to each other, to thereby detect a variation in voltage at a connection or intersection CS therebetween. Thus, it will be noted that the sensor device of FIG. 13 is provided with the n-type semiconductor detection element X3 in place of the resistor 31 in the sensor device of FIG. 4. The first detection element X2 functioning a P-type semiconductor may be formed of an organic semiconductor element such as lead phthalocyanine or an inorganic semiconductor element (a metal oxide element) such as nickel oxide, and the second detection element X3 functioning as an n-type semiconductor may be formed of an organic semiconductor element such as phthalocyanine having ruthenium and palladium incorporated therein or an inorganic semiconductor element (a metal oxide element) such as tin oxide.

When the sensor device shown in FIG. 13 is exposed to electron acceptor gas as produced in a flaming-type fire, the first detection element X2 which functions as a P-type semiconductor is decreased in resistance and the second detection element X3 which functions as an n-type semiconductor is increased in resistance. On the other hand, exposure of the sensor device to a smouldering-type fire causes the first P-type semiconductor detection element X2 to be increased in resistance and the second n-type semiconductor detection element X3 to be decreased in resistance.

Thus, a variation in voltage at the connection CS due to a variation in resistance of the detection elements X2 and X3 caused when the sensor device of FIG. 13 is exposed to electron acceptor gas or electron donor gas is increased double as compared with a variation in resistance across the resistor 31 in the sensor device of FIG. 4, so that the sensor device is highly increased in sensitivity in detection of gas. Also, when the second detection element X3 is formed of a semiconductor element which exhibits a variation in resistance due to a variation in temperature which is equal to that of the first detection element X2, a variation in resistance due to a variation in temperature is balanced between the first detection element X2 and the second detection element X3, so that the voltage at the connection CS is not affected or varied by a variation in temperature, resulting in detection of gas being carried out with highly increased reliability. In addition, the sensor device of the illustrated embodiment may be constructed in such a manner that leak characteristics of the first detection element X2 due to moisture are rendered substantially equal to those of the second detection element X3. Such construction effectively prevents leak characteristics of each of the detection elements X2 and X3 due to moisture from affecting the voltage at the connection CS between the detection elements X2 and X3, to thereby further improve reliability in detection of gas by the sensor device.

In the sensor devices shown in FIGS. 4 and 13, the elements exhibiting a function of a P-type semiconductor are used for the first detection elements X1 and X2. Alternatively, the elements exhibiting a function of a n-type semiconductor can be used for the first detection elements X1 and X2 (in this case, for the second detection element X3 in the sensor device of FIG. 13,the element exhibiting a function of a P-type semiconductor can be used). In the case where the element X1 is of a n-type semiconductor in FIG. 4, or the element X2 is of a n-type semiconductor and the element X3 is of a P-type semiconductor in FIG. 13, the sensor device is operated in such a manner that the first fire property signal Y2 is output during a smouldering-type fire, whereas the second fire property signal Y3 is generated during a flaming-type fire.

Figure 14:
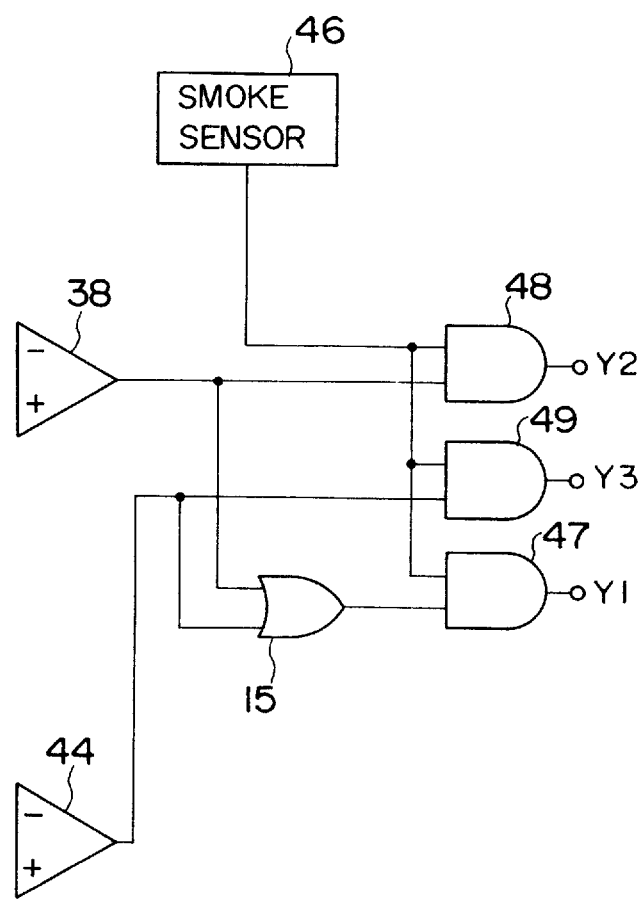
FIG. 14 is a circuit diagram showing a modification of an information output circuit.

Each of the detection elements described above exhibits increased sensitivity with respect to detectable gas. For example, there would be a possibility that each of the detection elements detects nitrogen dioxide in a concentration as low as ppb. Thus, it would be considered that the detection elements each are affected by miscellaneous gas existing in an environment, to thereby generate the fire occurrence signal Y1, the first fire property signal Y2 and the second fire property signal Y3, respectively. In order to avoid such erroneous detection due to high sensitivity of the detection elements, the information output circuit 14 of each of the sensor devices of FIGS. 4 and 13 may be constructed or modified, for example, in such a manner as shown in FIG. 14. More particularly, an information output circuit of FIG. 14 includes in addition to the components shown in FIG. 3, AND circuits 47, 48 and 49 for taking a logical AND between an output of a sensor 46 such as a conventional smoke sensor and an output of the OR circuit 15, a logical AND between the output of the sensor 46 and an output of the comparator 38, and a logical AND between the output of the sensor 46 and an output of the comparator 44 to output the fire occurrence signal Y1, first fire property signal Y2 and second fire property signal Y3, respectively. Thus, the information output circuit 14 shown in FIG. 14 is so constructed that the fire occurrence signal Y1, first fire property signal Y2 and second fire property signal Y3 are generated based on the discrimination result of each of the resistance decrease discriminator 12 and resistance increase discriminator 13 only when a predetermined result is output from the conventional sensor 46. Such construction of the circuit 14 shown in FIG. 14 permits an effect of miscellaneous gas in an environment on the detection element to be significantly reduced, to thereby improve reliability in detection of gas.

Also, there would be considered a possibility that a resistance of each of the detection elements is varied in a magnitude of the order of several digits. Thus, the resistance extractor 11 may be constructed so as to expand a dynamic range by means of a log amplification or the like or maintain the signal within a range which permits processing of the signal to be facilitated by means of an automatic gain controller. The construction of each of the resistance decrease discriminator 12 and resistance increase discriminator 13 shown in FIGS. 4 and 13 is described by way of an example, therefore, it is a matter of course that the discriminators 12 and 13 may be constructed in any other suitable way.

As described above, the sensor devices of the first and second embodiments each are so constructed that the information output circuit 14 may generate the fire occurrence signal Y1, first fire property signal Y2 and second fire property signal Y3. Alternatively, the information output circuit 14 may be constructed so as to generate only the fire occurrence signal Y1 or only the first fire property signal Y2 and second fire property signal Y3 depending on applications to which the sensor device is directed.

Figure 15:
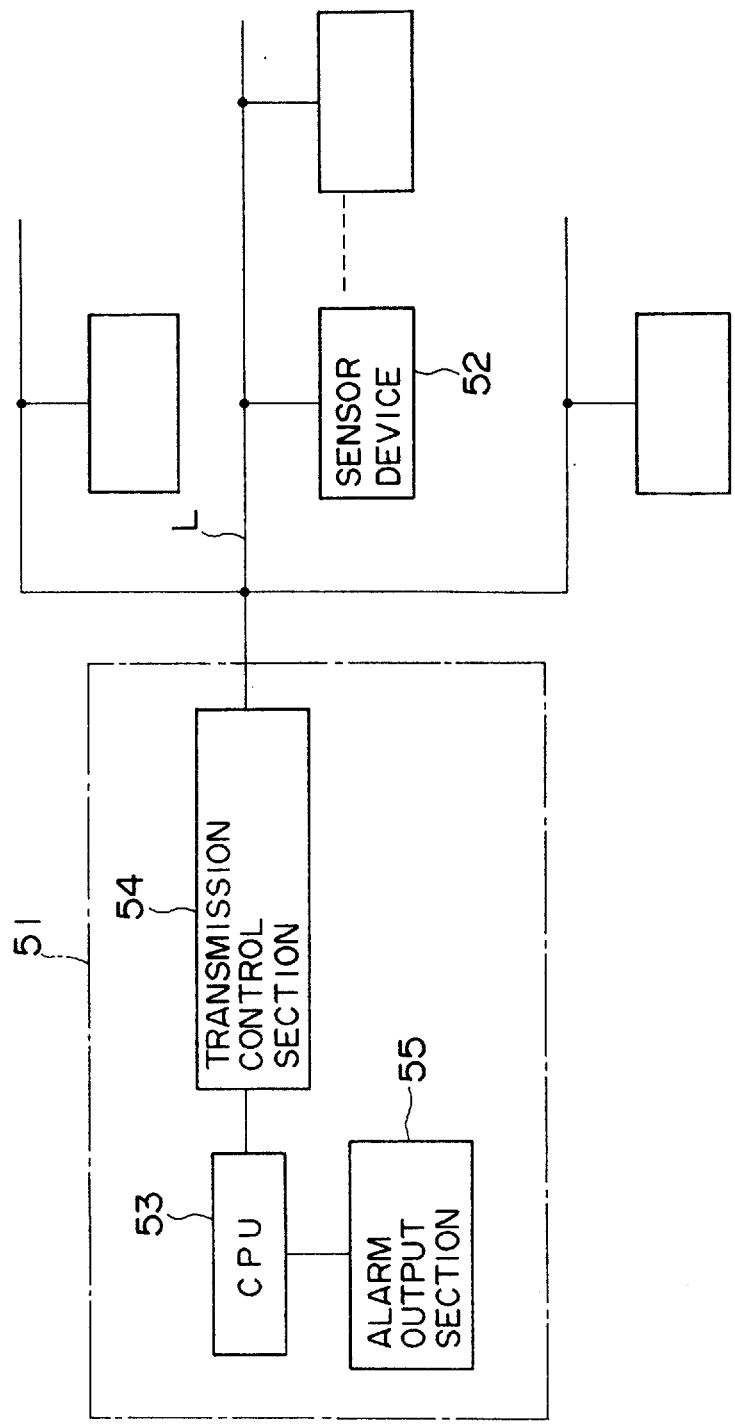
FIG. 15 is a block diagram showing a disaster prevention system in which a sensor device of the present invention is incorporated.

Referring now to FIG. 15, a disaster prevention system in which the sensor device shown in FIGS. 4 or 13 may be conveniently incorporated is illustrated. The disaster prevention system may be constructed in the form of, for example, a fire alarm system. The disaster prevention system shown in FIG. 15 includes a receiver 51 having a line L extending therefrom and a sensor device 52 constructed in such a manner as shown in FIGS. 4 or 13 and connected to the line L. The receiver 51 includes a central processing unit (CPU) 53, a transmission control section 54 which is adapted to carry out control of transmission between the section 54 and the sensor device 52, and an alarm output section 55. The sensor device 52 may be located, for example, at a predetermined position in a building.

Figure 16:
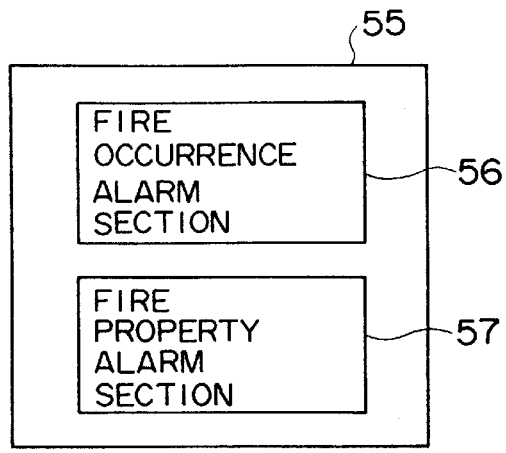
FIG. 16 is a block diagram showing an example of an alarm output section of a receiver.

When the disaster prevention system is constructed in the form of a fire alarm system, the alarm output section 55 of the receiver 51, as shown in FIG. 16, may include a fire occurrence alarm section 56 for alarming occurrence of a fire and a fire property alarm section 57 for alarming a type or property of the fire.

Now, the manner of operation of the disaster prevention system constructed as described above will be described hereinafter.

Supposing that a flaming-type fire occurs, the sensor device 52 generates a fire occurrence signal Y1 and a first fire property signal Y2. Based on the fire occurrence signal Y1 and first fire property signal Y2 output from the sensor device 52, the fire occurrence alarm section 56 and fire property output alarm section 57 of the receiver 51 may inform an operator of the fact that the fire occurs and a type or property of the fire is of a flaming-type, and/or may execute alarm control required when a flaming-type fire occurs. More particularly, when the first fire property signal Y2 indicating that the flaming-type fire occurs is output from the sensor device 52, the alarm output section 55 may rapidly control a fire-extinguishing equipment and promptly carry out escape guiding.

When a smouldering-type fire occurs, the sensor device 52 generates a fire occurrence signal Y1 and a second fire property signal Y3. Based on the signals Y1 and Y3, the fire occurrence alarm section 56 and fire property alarm section 57 of the receiver 51 inform an operator of the fact that the fire occurs and a type or property of the fire is a smouldering-type, and/or may execute alarm control required for smouldering-type fire. More particularly, when the second fire property signal Y3 indicating that the smouldering-type fire occurs is output from the sensor device 52, the alarm output section 55 may rapidly control a smoke discharge equipment, monitor the spread of the fire, and carry out escape guiding depending on progress of the fire.

In the case where the receiver 51 has a function of taking a logical OR between the first fire property signal Y2 and the second fire property signal Y3 to generate the fire occurrence signal Y1, the sensor device 52 may be constructed so as to permit the information output circuit 14 to output only the first fire property signal Y2 and second fire property signal Y3. Also, in the case where the alarm output section 55 of the receiver 51 merely has only a function of alarming occurrence of a fire, the sensor device 52 may be constructed so as to permit the information output circuit 14 to output only the fire occurrence signal Y1.

Figure 17:
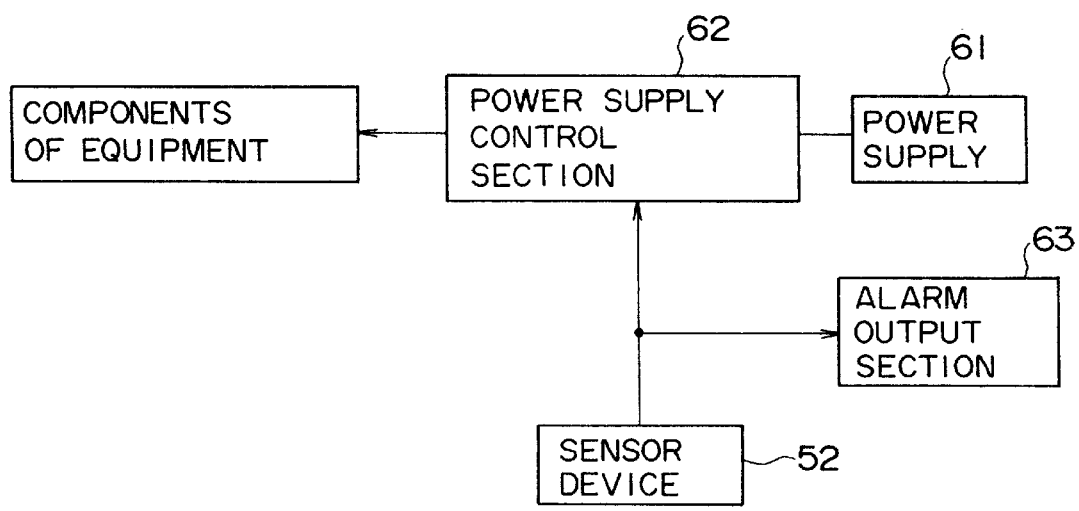
FIG. 17 is a block diagram showing an example of an electronic equipment in which a sensor device of the present invention is incorporated.

Referring now to FIG. 17, an electronic equipment having the sensor device shown in FIGS. 4 or 13 incorporated therein is illustrated. The electronic equipment shown in FIG. 17 includes a power supply section 61 for supplying components of the equipment with an electric power, a sensor device 52 constructed in such a manner as shown in FIGS. 4 or 13, a power supply control section 62 for controlling the power supply section 61 depending on signals output from an information output circuit incorporated in the sensor device 52, and an alarm output section 63 for outputting an alarm depending on signals output from the information output circuit. The information output circuit of the sensor device 52 may be constructed in the same manner as the information output circuit 14 described above with reference to FIG. 3 or FIG. 14.

FIG. 18 shows an embodiment of the electronic equipment generally constructed as shown in FIG. 17. In an electronic equipment of FIG. 18, a power supply control section 62 has a latching relay 64, which is adapted to receive a fire occurrence signal Y1 output from the information output circuit 14 of the sensor device 52. More particularly, the signal Y1 causes the latching relay 64 to be driven to interrupt supply of an electric power from the power supply section 61 to components of the equipment. It is a matter of course that the power supply control section 62 may comprise any suitable means other than the above-described latching relay. For example, it may comprise a means which functions to interrupt supply of an electric power from the power supply section 61 to the components for a predetermined period of time starting at the time when the fire occurrence signal Y1 is output from the sensor device 52.

In the electronic equipment shown in FIG. 18, the alarm output section 63 is adapted to receive the fire occurrence signal Y1, first fire property signal Y2 and second fire property signal Y3, to thereby alarm occurrence of a fire based on the signal Y1 and give information on a type or property of the fire based on the signals Y2 and Y3.

Now, the manner of operation of the electronic equipment of FIG. 18 constructed as described above will be described hereinafter.

In the electronic equipment, a detection section of the sensor device 52 is located so as to be exposed to gas produced when a fire occurs in the electronic equipment. The detection section may be formed of at least one organic semiconductor element or inorganic semiconductor element as in the detection element 1 described above with reference to FIGS. 1(a) to 2(b).

When a flaming-type fire occurs in the electronic equipment, the fire occurrence signal Y1 and the first fire property signal Y2 are output from the sensor device 52. On the other hand, when a smouldering-type fire occurs in the electric equipment, the fire occurrence signal Y1 and the second fire property signal Y3 are output from the sensor device 52. Thus, whenever any type of fire occurs, the latching relay 64 receives the fire occurrence signal Y1 to interrupt supply of an electric power from the power supply 61 to the components of the equipment. Together with this, the alarm output section 63 receives the signals Y1, Y2 and Y3 to output information on occurrence of the fire and a type or property of the fire as to whether the fire is a flaming-type or a smouldering-type in the same manner as the alarm output section 55 of the receiver 51 of the disaster prevention system shown in FIG. 12. Also, the signals Y1,Y2 and Y3 permit the alarm output section 63 to carry out alarm control required.

A fire sensor which is conventionally incorporated in such an electronic equipment as described above includes a heat sensor such as a bimetal element for detecting a temperature, an ionization-type smoke sensor, and a photoelectric-type smoke sensor. The heat sensor has a significant defect of failing to exhibit sensitivity to a smouldering-type fire because it is constructed so as to detect only heat. The ionization-type smoke sensor is required to be formed into a size as large as a distance of travel of a particles from α radiation source for the purpose of ionization of smoke in an ion chamber in which measurement of the smoke is carried out, resulting in failing to be significantly down-sized. Also, the ionization-type smoke sensor exhibits another problem of rendering disposal of the sensor highly troublesome because it utilizes radioactive rays. It has a further defect of failing to exhibit satisfactory sensitivity to a smouldering-type fire occurring due to abnormal heating of components or parts of the equipment. In the photoelectric-type sensor, it is required in view of signal processing to keep a ratio between a scattered light signal by smoke and noise light signal reflected on an inner surface of a black box at a certain value according to a principle based on a scattered light system, resulting in failing to down-size the black box. Also, the photoelectric-type sensor has an additional problem of being increased in manufacturing cost and complicated in construction, because it is required to arrange an amplifier of high gain in a circuit thereof in view of the fact that the scattered light signal is highly weak or feeble and a pulse drive circuit is required for power-saving.

Also, a gas sensor which is formed of a metal oxide or the like has been conventionally known in the art. However, such a gas sensor fails to detect any abnormal property because it is constructed so as to merely detect occurrence of abnormality on specific gas.

Unlike the above-described conventional fire sensors, the sensor device of the present invention permits not only both a flaming-type fire and a smouldering-type fire to be detected, but a type or property of each of the fires to be detected, so that incorporation of the sensor device of the present invention in an electronic equipment results in disaster control being surely accomplished.

Further, in the conventional gas sensor constructed of a metal oxide or the like, it is required to heat the sensor itself in order to permit the sensor to react on only specific or predetermined gas to enhance selectivity or sensitivity to the specific gas.

More particularly, the conventional gas sensor formed of a metal oxide or the like is adapted to detect only specific gas or electron donor gas based on a principle that when the metal oxide is heated to a temperature of 200° to 300° C. by a high-temperature heating unit, only electron donor gas reacts with the metal oxide to cause a resistance of the metal oxide to be decreased, while electron acceptor gas does not substantially react with the metal oxide (the resistance of the metal oxide being substantially kept unvaried).

On the contrary, the sensor device of the present invention has been made taking notice of the fact that the detection element which is formed of an inorganic semiconductor element of a metal oxide such as nickel oxide, tin oxide or the like is varied in resistance by both electron acceptor gas and electron donor gas, and the fact that a variation in resistance of the detection element caused by electron acceptor gas is different in polarity from that by electron donor gas. Thus, the detection element of the present invention permits not only occurrence of abnormality such as a fire but a type or property of the abnormality to be detected. For this purpose, it is required that the metal oxide is placed under a temperature condition which permits it to exhibit properties of reacting with both electron acceptor gas and electron donor gas.

Such properties of the detection element fail to appear when the metal oxide is heated to a temperature of about 200° to 300° C. More particularly, when the metal oxide is heated to such a high temperature, it is caused to substantially react with only any one of electron acceptor gas and electron donor gas, to thereby fail to surely react with both gases.

Thus, the sensor device of the present invention, even when it includes the detection element formed of the metal oxide, permits the metal oxide to effectively react with both electron acceptor gas and electron donor gas without being heated to a high temperature and requiring any high-temperature heating unit as in the conventional gas sensor.

Likewise, the sensor device of the present invention, even when it includes the detection element formed of the organic semiconductor element, permits the detection element to exhibit high sensitivity to both electron acceptor gas and electron donor gas without being heated. Thus, it will be noted that the sensor device of the present invention in which the detection element is formed of the organic semiconductor element or inorganic semiconductor element exhibits high sensitivity as compared with the conventional smoke sensor and detects not only occurrence of a fire but a property or type of the fire without requiring any specific heating device and being heated to a high temperature, resulting in effectively detecting an initial state of a fire irrespective of a type of the fire to interrupt a power supply of the electronic equipment, to thereby previously prevent a fire due to electrical abnormal heating.

Also, the sensor device of the present invention using the organic semiconductor element or inorganic semiconductor element, as described above, may be down-sized as compared with the conventional sensor, therefore, it can be located at any desired position, accomplish energy saving and a decrease in manufacturing cost, and provide an electronic equipment for mass production with a satisfactory disaster prevention function. In particular, the organic semiconductor element and inorganic semiconductor element may be down-sized, therefore, an electronic equipment is prevented from being large-sized even when the sensor device is incorporated in the electronic equipment by arranging the detection element on a circuit board of the equipment on which required circuit elements are mounted.

The foregoing description on the organic semiconductor element used in the present invention has been made on phthalocyanines such as, for example, metal substituted phthalocyanines, metal substituted phthalocyanines to which metal oxides are added, or the like, however, the organic semiconductor element is not limited to such phthalocyanines. For example, the organic semiconductor element may be formed of conductive polymers such as polypyrrole which is doped with ions or the like. Use of such conductive polymers for the organic semiconductor element permits the detection element to likewise exhibit the above-described advantages.

Further, in the embodiments described above, the inorganic semiconductor element is formed of a metal oxide such as nickel oxide, tin oxide or the like, however, it may be formed of any suitable metal oxide mixture such as a mixture of nickel oxide and tin oxide, or the like. Alternatively, a combination of any of the metal oxides with a catalyst of noble metal such as Pt, Pd, Ru or the like and/or a binder such as alumina, silica or the like may be used for this purpose.

In addition, it is known that water vapor acts as electron donor gas, therefore, the organic semiconductor element may be formed of phthalocyanine having a hydrophobic functional group attached thereto in order to substantially reduce or minimize an effect of moisture on the organic semiconductor element. Alternatively, resistance to moisture of the organic semiconductor element may be increased by mixing alkane and phthalocyanine with a solvent and then applying the mixed solvent to a substrate of the organic semiconductor element.

Figure 19A:
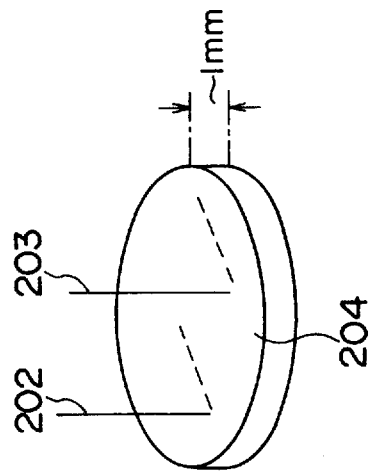
FIGS. 19(a) to 19(c) each are a schematic view showing a construction of a detection element.
Figure 19B:
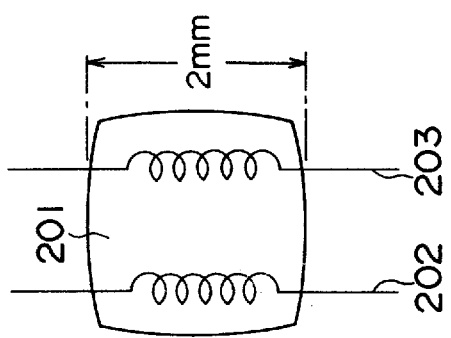
Figure 19C:
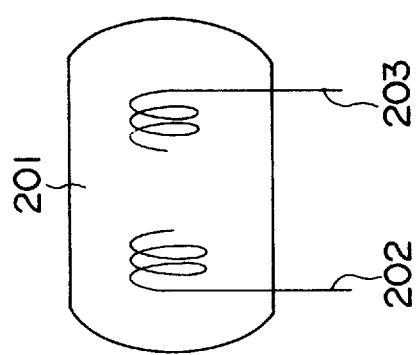

The above description of the detection element of the present invention has been made in connection with such a comb electrode structure as shown in FIGS. 1(a) and 1(b), however, the detection element may be constructed into any suitable electrode structure other than the comb structure. For example, the detection element of the present invention may be constructed to be in such a structure as shown in each of FIGS. 19(a) to 19(c) each showing a conventional gas sensor. The structure shown in each of FIGS. 19(a) and 19(b) is constructed by pouring a paste 201 formed of a mixture of a gas sensitive semiconductor and a solvent into a space between electrodes 202 and 203 each made of platinum to surround the electrodes 202 and 203 with the mixed paste and subjecting the paste to curing and sintering, to thereby provide a detection element. The structure shown in FIG. 19(c) may be constructed by pouring a gas sensitive semiconductor material 204 between electrodes 202 and 203 and hardening it under pressure, to thereby provide a detection element.

The above description of the detection element used in the present invention for detecting occurrence of abnormality and/or a type or property of the abnormality has been made on the organic semiconductor element or inorganic semiconductor element. However, the detection element used in the present invention is not limited to the organic and inorganic elements. The detection element may be formed of any suitable material other than the above-described organic and inorganic materials so long as it can be varied in characteristic value by both electron acceptor gas and electron donor gas and cause a variation in characteristic value of the detection element by electron acceptor gas to be different in polarity from that by electron donor gas.

Furthermore, in the embodiments described above, a resistance of the detection element is used as an example of a characteristic value of the detection element. However, the characteristics of the detection element may be represented by any suitable characteristic value other than the resistance so long as a variation thereof by electron acceptor gas is different in polarity from that by electron donor gas. For example, when a capacitance of the detection element is varied by both electron acceptor gas and electron donor gas and a variation in capacitance of the detection element by electron acceptor gas is different in polarity from that by electron donor gas, the capacitance may be used as a representative of the characteristic value. When a capacitance of the detection element is used as the characteristic value, the characteristic value monitoring section 2 may include an oscillation circuit for detecting a variation in capacitance of the detection element.

Moreover, the above description has been made on the detection element which is adapted to react with electron acceptor gas produced by a flaming-type fire and electron donor gas produced by a smouldering-type fire, however, the present invention is not limited to the above description. For example, the detection element used in the present invention may have characteristics contrary to the above. More particularly, the detection element may be constructed so as to react with electron donor gas produced by a flaming-type fire and electron acceptor gas produced by a smouldering-type fire.

As can be seen from the foregoing, the present invention is constructed so as to detect abnormality and/or a type or property of the abnormality by means of the detection element wherein a characteristic value of the detection element is varied by both electron acceptor gas and electron donor gas and a variation in characteristic value of the detection element caused by electron acceptor gas is different in polarity from that caused by electron donor gas. Such construction of the present invention permits the detection element to positively detect occurrence of abnormality such as a fire irrespective of a type of the abnormality and effectively discriminate a type or property of the abnormality.

While preferred embodiments of the invention have been described with a certain degree of particularity with reference to the drawings, obvious modifications and variations are possible in light of the above teachings. It is therefore to be understood that within the scope of the appended claims, the invention may be practiced otherwise than as specifically described.

What is claimed is:

1. A sensor device comprising one detection element made of a substrate, a semiconductor layer on said substrate, and spaced-apart electrodes in contact with said semiconductor layer, wherein said semiconductor layer is selected to be of a given conductivity type and has a property of varying a predetermined characteristic value thereof in one direction of polarity in response to exposure of said detection element to electron acceptor gas produced by a flaming type of fire and of varying the predetermined characteristic value thereof in an opposite direction of polarity in response to exposure of said detection element to electron donor gas produced by a smouldering type of fire, and characteristic value discrimination means coupled to the electrodes of said one detection element which discriminates a variation in the predetermined characteristic value thereof in the one polarity direction as being produced by electron acceptor gas indicating a flaming type of fire, and discriminates a variation of the predetermined characteristic value in the other polarity direction as being produced by electron donor gas indicating a smouldering type of fire, so that occurrences of both types of fires which generate the two different kinds of gases may be detected by said one detection element.

2. A sensor device according to claim 1, wherein organic semiconductor elements including metal substituted phthalocyanines, metal substituted phthalocyanines to which metal oxides are added, or ion-doped polymers are used as said detection element, or inorganic semiconductor elements including a metal oxide having electric conductivity of a semiconductor level are used as said detection element.

3. An electronic equipment according to claim 1, further comprising a power supply for supplying an electric power to components of said electronic equipment;

wherein said power supply is operated so as to interrupt supply of the electric power to said components of said electronic equipment when said sensor device detects fire.

4. A sensor device according to claim 1, wherein said sensor device is provided with:

a detection means including said one detection element; and said characteristic value discriminating means is coupled to characteristic monitoring means which outputs a fire occurrence signal and a fire type signal depending on the variation in predetermined characteristic value of said detection element.

5. A sensor device according to claim 4, wherein the characteristic value of said one detection element is a resistance which increases upon exposure to one of said first and second kinds of gas and decreases upon exposure to the other of said first and second kinds of gas; and said characteristic monitoring means includes a resistance decrease discriminating means for discriminating whether the resistance extracted from said detection element is decreased by a predetermined amount within a predetermined time period, a resistance increase discriminating means for discriminating whether the resistance extracted is increased by a predetermined amount within a predetermined time period, and an information output means for outputting said fire occurrence and type signals depending on a discrimination result provided by each of said resistance decrease discriminating means and resistance increase discriminating means.

6. A sensor device according to claim 5, wherein said information output means includes an abnormality occurrence output means for outputting abnormality occurrence information at any time when said resistance decrease discrimination means provides a discrimination result indicating a decrease in resistance or when said resistance increase discrimination means provides a discrimination result indicating an increase in resistance.

7. A sensor device according to claim 5, wherein said information output means includes an abnormality property output means for outputting first abnormality property information when said resistance decrease discrimination means provides a discrimination result indicating a decrease in resistance and for outputting second abnormality property information when said resistance increase discrimination means provides a discrimination result indicating an increase in resistance.

8. A sensor device according to claim 5, further including a conventional sensor providing a detection result, and wherein said information output means combines the detection result provided by the conventional sensor with the discrimination results provided by said resistance decrease discrimination means and resistance increase discrimination means to output said fire occurrence and type signals.

9. A sensor device according to claim 4, wherein said one detection element is a first detection element of a predetermined first conductivity type and said sensor device includes a second detection element of a predetermined second conductivity type opposite to said first conductivity type which is connected in series therewith, each of said first and second detection elements being made of a material having a property of varying a resistance thereof in one direction of polarity in response to electron acceptor gas and of varying the resistance thereof in an opposite direction of polarity in response to electron donor gas, and said first and second detector elements being electrically connected to each other in a manner so as to double the response of the resistance extracted in each direction of polarity; and wherein said characteristic monitoring means includes a resistance decrease discriminating means for discriminating whether the resistance extracted is decreased by a predetermined amount within a predetermined period of time, a resistance increase discriminating means for discriminating whether the resistance extracted is increased by a predetermined amount within a predetermined period of time, and an information output means for outputting said fire occurrence and type signals depending on a discrimination result provided by each of said resistance decrease discriminating means and resistance increase discriminating means.

10. An electronic equipment according to claim 9, wherein detection elements used in said sensor device are mounted on circuit boards on which electric circuits for said electronic equipment are mounted.

* * * * *